US00PP26691P3

(12) United States Plant Patent
Sato et al.

(10) Patent No.: US PP26,691 P3
(45) Date of Patent: May 3, 2016

(54) **NEW GUINEA *IMPATIENS* PLANT NAMED 'SAKIMP019'**

(50) Latin Name: *Impatiens hybrida hort*
Varietal Denomination: SAKIMP019

(71) Applicant: Sakata Seed Corporation, Yokohama (JP)

(72) Inventors: Chihiro Sato, Nagano (JP); Chuichi Tsukada, Nagano (JP)

(73) Assignee: Sakata Seed Corporation, Yokohama (JP)

( * ) Notice: Subject to any disclaimer, the term of this patent is extended or adjusted under 35 U.S.C. 154(b) by 171 days.

(21) Appl. No.: 13/998,936

(22) Filed: Dec. 23, 2013

(65) Prior Publication Data

US 2015/0181792 P1 Jun. 25, 2015

(51) Int. Cl.
*A01H 5/02* (2006.01)

(52) U.S. Cl.
USPC ..... Plt./318.4

(58) Field of Classification Search
USPC ..... Plt./318.4
See application file for complete search history.

*Primary Examiner* — Keith Robinson
(74) *Attorney, Agent, or Firm* — Barbara Campbell; Bethany R. Roahrig; Cochran Freund & Young, LLC

(57) ABSTRACT

A New Guinea *Impatiens* plant particularly distinguished by having a pink flower color, strong root system and a compact plant growth habit, is disclosed.

1 Drawing Sheet

Genus and species: *Impatiens hybrida hort.*
Variety denomination: 'SAKIMP019'.

BACKGROUND OF THE NEW PLANT

The present invention comprises of a new and distinct cultivar of New Guinea *Impatiens*, botanically known as *Impatiens hybrida hort*, and referred to by the variety name 'SAKIMP019'. 'SAKIMP019' originated from a hybridization in June 2006 in Misato, Japan between the proprietary female *Impatiens* breeding line 'NF-11' (unpatented) having an orange flower color and the proprietary male *Impatiens* breeding line 'NF-456A' (unpatented) having a magenta flower color.

In June 2006, the female parent line 'NF-11' and male parent line 'NF-456A' were crossed and a population of $F_1$ plants was created. The $F_1$ plants were evaluated in Misato, Japan in an open field trial. The criteria for plant selection included a pink flower color, strong root system and a compact plant growth habit. At the completion of the trial, one single-plant selection was made based on the above criteria and vegetatively propagated. From May to August 2008, the selection was evaluated in an open field in Misato, Japan. Terminal tip vegetative cuttings of the variety were then shipped to Salinas, Calif., where the plants were regenerated and reevaluated for stability of traits. The selection subsequently was named 'SAKIMP019' and was found to have its unique characteristics reproduce true to type in successive generations of asexual propagation via terminal tip vegetative cuttings in Salinas, Calif.

SUMMARY

The following are the most outstanding and distinguishing characteristics of this new variety when grown under normal horticultural practices in Salinas, Calif.

1. Pink flowers;
2. Strong root system; and
3. A compact plant growth habit.

DESCRIPTION OF THE PHOTOGRAPHS

This *Impatiens* plant is illustrated by the accompanying photographs which show the plant's overall plant habit including form, foliage, and flowers. The photographs are of plants grown about 3.5 months from propagation by terminal tip vegetative cuttings in Salinas, Calif. under greenhouse conditions in the summer of 2013. The colors shown are as true as can be reasonably obtained by conventional photographic procedures.

DESCRIPTION OF THE NEW VARIETY

Figure 1:
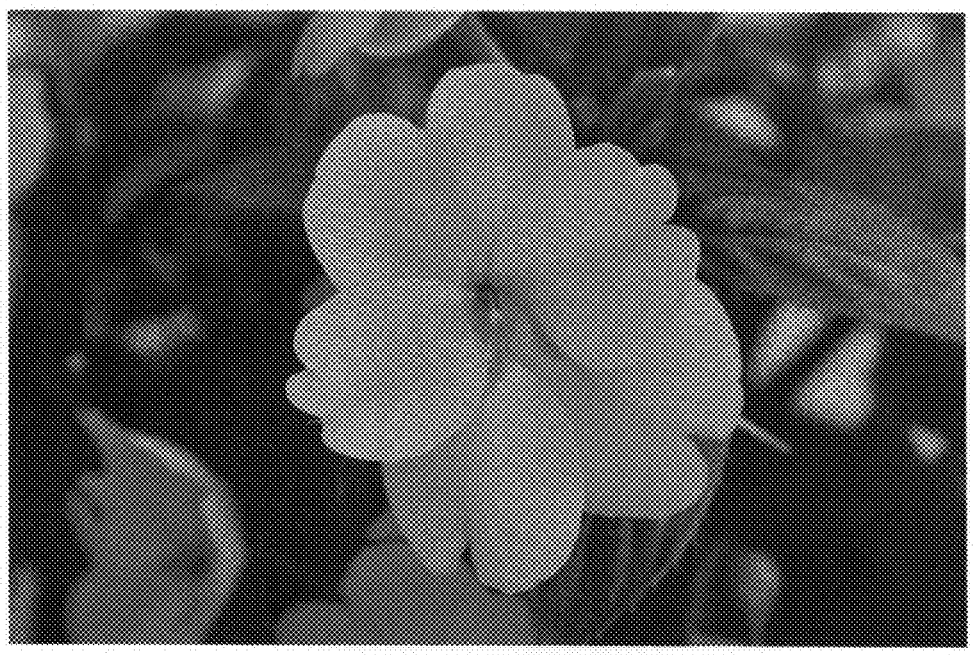
FIG. 1 shows a close-up of the mature inflorescence of the plant.
Figure 2:
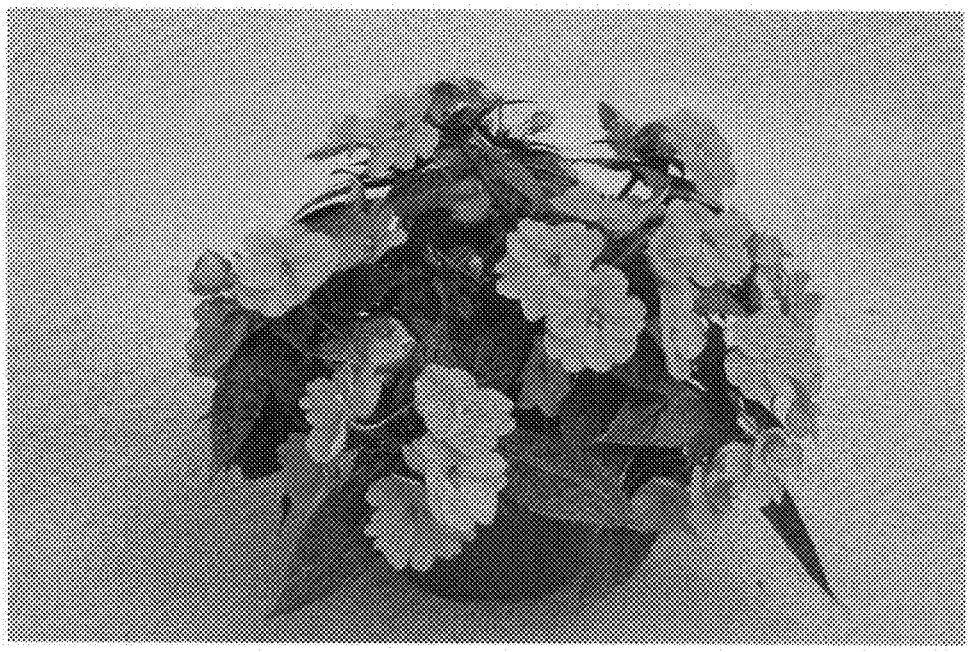
FIG. 2 shows the overall plant habit of the plant grown in a pot.

The following detailed descriptions set forth the distinctive characteristics of 'SAKIMP019'. The data which define these characteristics were collected from asexual reproductions carried out in Salinas, Calif. Data was collected on plants grown about 3.5 months from propagation by terminal cuttings under greenhouse conditions in Salinas, Calif. in the summer of 2013. Color references are to The R.H.S. Colour Chart of The Royal Horticultural Society of London (R.H.S.), $4^{th}$ edition (2001).

Classification:

*Family*.—Balsaminaceae.

*Botanical*.—*Impatiens* interspecific cross (*Impatiens hybrida hort*).

*Common*.—*Impatiens*.

*Designation*.—'SAKIMP019'.

Parentage:

*Female parent*.—Proprietary *Impatiens* line 'NF-11' (unpatented).

*Male parent*.—Proprietary *Impatiens* line 'NF-456A' (unpatented).

Growth:

*Time to produce a rooted cutting*.—About 4 weeks.

*Time to initiate roots*.—2 weeks.

*Rooting habit*.—Vigorous.

*Root type*.—Fibrous.

*Root color*.—RHS 155A (White).

*Environmental conditions for plant growth*.—The terminal 1.0 to 1.5 inches of an actively growing stem was excised. The vegetative cuttings were propagated in five to six weeks. The base of the cuttings were dipped for 1 to 2 seconds in a 1:9 solution of DIP 'N GROW (1 solution: 9 water) a root inducing solution, immediately prior to sticking into the cell trays. Cuttings were stuck into plastic cell trays having 98 cells, and containing a moistened peat moss-based growing medium. The cuttings were misted with water from overhead for 10 seconds every 30 minutes until sufficient roots were formed. Rooted cuttings were transplanted and grown in 6-inch plastic pots in a glass greenhouse located in Salinas, Calif. Pots contained a peat moss-based growing medium. Soluble fertilizer containing 20% nitrogen, 10% phosphorus and 20% potassium was applied once a day or every other day by overhead irrigation. Plants were fertilized every 2 to 3 days, 2 times in consecutive applications and then given one clear water application. Pots were top-dressed with a dry, slow release fertilizer containing 14% nitrogen, 14% phosphorus and 14% potassium. The typical average air temperature was 24° C. Time to bloom from propagation: 6 to 8 weeks.

Plant description:

*Habit*.—Compact.

*Life cycle*.—Tender perennial.

*Height* (*from soil line to top of foliage*).—20.0 cm to 21.0 cm.

*Spread*.—37.0 cm to 38.0 cm.

*Flowering requirements*.—Will flower so long as temperature is above 5° C.

*Temperature tolerances*.—Plants observed to continue flowering in a temperature range of 5° C. to 36° C. Plants can withstand high heat and humidity.

Branches:

*Number of branches*.—3 main branches.

*Length of branches*.—Approximately 2.0 cm from soil line to first node, approximately 2.0 cm from first node to second node, approximately 13.0 cm to 14.0 cm total.

*Diameter of branches*.—0.5 cm for the main branch.

*Color of branches*.—RHS 187B (Greyed-Purple).

*Texture*.—Smooth.

Stems:

*General description*.—Strong; circular cross-section, smooth and shiny.

*Stem length*.—10.0 cm.

*Diameter*.—0.6 cm.

*Internode length*.—4.0 cm.

*Color*.—RHS 146C (Yellow-Green) with specks of RHS 187A (Greyed-Purple).

*Pubescence*.—Absent.

*Anthocyanin color*.—RHS 187A (Greyed-Purple).

Leaves:

*Arrangement*.—Whorled, with up to 5 leaves per node, opposite if only two leaves at one node.

*Shape*.—Lanceolate, curled.

*Apex*.—Acuminate.

*Base*.—Attenuate.

*Margin*.—Ciliate.

*Surface appearance* (*both surfaces*).—Dull, waxy.

*Surface pubescence* (*both surfaces*).—Absent; surface is glabrous.

*Length*.—14.0 cm.

*Width*.—6.0 cm.

*Color*.—Upper surface: Closest to RHS N189A (Greyed-Green). Lower surface: RHS 189A (Greyed-Green) with specks of RHS 187B (Greyed-Purple) and RHS 187B (Greyed-Purple) veins.

*Texture* (*both surfaces*).—Glabrous.

*Venation*.—Pinnate.

*Venation color*.—Upper surface: RHS 187D (Greyed-Purple). Lower surface: RHS 187B (Greyed-Purple).

*Variegation*.—Absent.

*Fragrance*.—Absent.

*Petiole*.—Length: 2.5 cm. Diameter: 0.3 cm. Color: RHS 187D (Greyed-Purple). Texture: Smooth, glabrous. Strength: Medium.

Flowers:

*Total number of flowers per node*.—1 to 3 in bloom, about 4 to 6 flower buds per node.

*Total number of flower per plant*.—Approximately 35 in bloom.

*Inflorescence type*.—Single flower with spur.

*Lastingness of individual blooms on the plant*.—14 days.

*Fragrance*.—Absent.

*Pedicel*.—Absent.

Flower bud:

*Surface texture*.—Glabrous.

*Length*.—2.0 cm.

*Diameter*.—1.3 cm.

*Shape*.—Deltoid, longitudinal cross-section.

*Color*.—RHS 58C (Red-Purple).

Peduncle:

*Length*.—4.0 cm.

*Diameter*.—0.3 cm.

*Color*.—RHS 149D (Yellow-Green).

*Surface texture*.—Glabrous, smooth.

*Strength*.—Medium.

Corolla:

*Shape*.—Roughly circular with 5 radial petals.

*Diameter*.—Approximately 6.5 cm.

*Depth*.—0.5 cm.

*Petals*.—Shape: Obcordate. Apex: Emarginate (cleaved). Base: Attenuate. Margin: Entire. Pubescence (both surfaces): Glabrous. Length: 4.0 cm. Width: 3.8 cm. Color: Upper: RHS 58C (Red-Purple). Lower: RHS 58D (Red-Purple). Eye zone: RHS 53C (Red).

Spur:

*Shape*.—Tubular; curved downward.

*Length*.—6.5 cm.

*Diameter*.—0.2 cm.

*Color*.—Closest to RHS 54B (Red).

*Texture*.—Smooth.

*Degree of curvature*.—Medium.

Calyx:

*Arrangement*.—Composed of 2 sepals.

*Sepals*.—Shape: Lanceolate. Apex: Caudate. Base: Subcordate. Margin: Entire. Surface texture (both surfaces): Glabrous. Color: RHS 58A (Red-Purple) and RHS 141D (Green). Length: 1.5 cm. Diameter: 0.8 cm.

Reproductive organs:

*Stamen number*.—Approximately 5 to 10 but too tiny to count; stamens are united in an asymmetrical tube surrounding the ovary.

*Stamen form*.—Fused; split into 4 lobes.

*Filament length*.—0.5 cm.

*Filament color*.—RHS 54C (Red).

*Anther length*.—0.4 cm.

*Anther color*.—RHS 155A (White).

*Pollen color*.—RHS 155A (White).

*Pollen amount*.—Abundant.

*Pollen description*.—Powdery.

*Ovary arrangement*.—Parietal.

*Ovary surface color*.—RHS 143A (Green).

*Pistil number*.—5.

*Stigma color*.—RHS 143A (Green).

*Style length*.—0.5 cm.

*Style color*.—RHS 143A (Green).

*Seed production*.—Absent.

Disease and insect resistance: No particular resistance or susceptibility observed.

COMPARISON WITH PARENTAL LINES AND KNOWN VARIETY

'SAKIMP019' is a new and unique variety of *Impatiens* owing to its pink flower color, strong root system and a compact plant growth habit. 'SAKIMP019' is distinguished from its parents mainly by flower color as shown in Table 1 below:

TABLE 1

Comparison with Parental Lines

| Characteristic | 'SAKIMP019' | Female Parent 'NF-11' | Male Parent 'NF-456A' |
|---|---|---|---|
| Flower color | Pink | Orange | Magenta |

'SAKIMP019' is a new and unique variety of *Impatiens* owing to its pink flower color, strong root system and a compact plant growth habit. 'SAKIMP019' is most similar to the commercial *Impatiens* variety 'SAKIMP013' (U.S. Plant Pat. No. 19,597), commercially known as SUNPATIENS® 'Compact Blush Pink'; however there are differences as described in the table below.

TABLE 2

Comparison with Similar Variety

| Characteristic | 'SAKIMP019' | 'SAKIMP013' |
|---|---|---|
| Petal color, upper surface | RHS 58C (Red-Purple) | RHS 65C (Red-Purple) |
| Petal color, lower surface | RHS 58D (Red-Purple) | RHS 65C (Red-Purple) |
| Petal color, eye zone | RHS 53C (Red) | RHS 67C (Red-Purple) |

We claim:

1. A new and distinct variety of New Guinea *Impatiens* plant as shown anal described herein.

* * * * *